United States Patent [19]

Maryanoff et al.

[11] Patent Number: 5,258,525
[45] Date of Patent: Nov. 2, 1993

[54] PROCESSES FOR PREPARING [2S-(2α,3Aβ,7Aβ)]OCTAHYDRO-1H-INDOLE-2-CARBOXYLIC ACID AND ESTERS

[75] Inventors: Cynthia A. Maryanoff, New Hope; Cynthia L. Fedde, Warrington; Robin C. Stanzione, King of Prussia; Frank J. Villani, Jr., Perkasie, all of Pa.

[73] Assignee: McNeilab, Inc., Spring House, Pa.

[21] Appl. No.: 675,786

[22] Filed: Mar. 27, 1991

[51] Int. Cl.⁵ .......................................... C07D 209/04
[52] U.S. Cl. .................................................... 548/452
[58] Field of Search ........................................ 548/452

[56] References Cited

PUBLICATIONS

CA 109:231529qg Synthesis . . . 59780. Pichat et al., p. 915, 1988.
Journal of Labelled Compounds and Radiopharmaceuticals—vol. XXV, No. 5 Pichat et al., 1988.

*Primary Examiner*—Mary C. Lee
*Assistant Examiner*—Joseph K. McKane
*Attorney, Agent, or Firm*—Joseph J. Brindisi

[57] ABSTRACT

The processes provide for the preparation of a [2S-(2α, 3aβ, 7aβ)]-octahydro-lH-indole-2-carboxylic ester from an ester precursor by a stereospecific hydrogenation at a pressure below about 400 psi. In addition, the processes provide for the preparation of [2S-(2αm 3aβ, 7aβ)]-octahydro-lH-indole-2-carboxylic acid or a ester thereof by the hydrogenation of a (2S)-2-carboxyindoline acid precursor.

7 Claims, No Drawings

PROCESSES FOR PREPARING [2S-(2α,3Aβ,7Aβ)]OCTAHYDRO-1H-INDOLE-2-CARBOXYLIC ACID AND ESTERS

FIELD OF THE INVENTION

This invention relates to improved and novel processes for synthesizing [2S-(2α, 3aβ, 7aβ)]-octahydro-1H-indole-2-carboxylic acid and esters of the formula I:

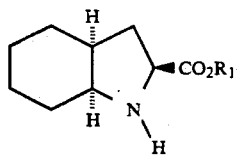

by the stereospecific catalytic hydrogenation of either (2S)-2-carboxyindoline, (2S)-2-carbalkoxyindoline or their protic acid salts at pressures below about 400 psi. The compounds are useful as intermediates in the preparation of inhibitors of angiotensin converting enzyme (ACE), which are employed in treating hypertension.

BACKGROUND OF THE INVENTION

Processes for preparing individual racemic (2α, 3aβ, 7aβ)-octahydro-1H-indole-2-carboxylic acid and esters species are known.

U.S. Pat. No. 4,350,704 and Blankley et. al. (*J. Med. Chem.*, 30, 992 (1987) disclose that ethyl indole-2-carboxylate, is hydrogenated in a Paar apparatus

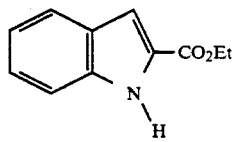

in a reaction medium containing absolute ethanol and concentrated sulfuric acid with 10% rhodium on charcoal or 10% rhodium on carbon respectively to yield a racemic mixture of ethyl (2α, 3aβ, 7aβ)-octahydro-1H-indole-2-carboxylate. That racemic mixture is resolved through classic multistep procedures i.e. it is then de-esterified, benzoylated, fractionally crystallized as an α-methylbenzylamine salt and de-benzoylated to yield individual enantiomeric acid species or the mixture is de-esterified, re-esterified, fractionally crystallized as a tartrate salt then de-esterified and basified to yield individual enantiomeric ester species.

U.S. Pat. No. 4,508,729 (hereinafter "the '729 Patent") discloses that the hydrochloride salt of ethyl (2S)-indoline-2-carboxylate is stereospecifically hydrogenated at a high pressure of 50 kg/cm²( 711 psi). The reaction takes place in water using Palladium on charcoal to yield the hydrochloride salt of ethyl [2S-(2α,-3aβ,7aβ)]-octahydro-1H-indole-2-carboxylate.

The stereospecific hydrogenation of the hydrochloride salt of ethyl (2S)-indoline-2-carboxylate is also disclosed in *Tetrahedron Lett.*, 23(16), 1677 (1982), which authors include all of inventors of the '729 Patent. The reference, however, only superficially discloses details regarding the reaction (i.e., that it occurs in ethanol using palladium on carbon to yield the hydrochloride salt of ethyl [2S-(2α,3aβ,7aβ)-octahydro-1H-indole-2-carboxylic ester and that the ester is saponified to the corresponding acid employing a sodium hydroxide solution of water and ethanol).

None of these publications, however, disclose a process for preparing a [2S-(2α, 3aβ, 7aβ)]-octahydro-1H-indole-2-carboxylate ester from an ester precursor by a stereospecific hydrogenation at a pressure below 700 psi. In addition, there is no disclosure of a process for preparing [2S-(2α,3aβ,7aβ)]-octahydro-H-indole-2-carboxylic acid or its ester by the hydrogenation of a (2S)-2-carboxyindoline acid precursor.

SUMMARY OF THE INVENTION

The invention relates to improved and novel processes for synthesizing [2S-(2α,3aβ,7aβ)]-octahydro-1H-indole-2-carboxylic ester and esters of the formula I

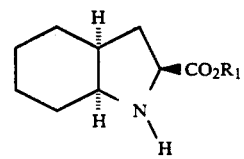

wherein $R_1$ is selected from any of H, $C_{1-6}$ straight- or branched-chained alkyl and $C_{4-6}$ cycloalkyl.

The ester compounds of formula I are prepared at a Pressure below about 400 psi by using a precious metal based catalyst containing more than about 5% by weight of the precious metal based on the weight of the catalyst to hydrogenate either (2S)-2-carboxyindoline, (2S)-2-carbalkoxyindoline or their protic acid salts. The hydrogenation is effected in a acidified and deoxygenated solvent such as an alcohol, which contains no more than a minimal amount of water. The solvent is acidified with a sufficient amount of acid such that the added acid is in excess of the amount of acid required to protonate the equivalent amount of the reactant indoline species.

The acid compound of formula I is formed either by hydrolyzing the aforesaid formed esters or, preferably, by the one step hydrogenation of either (2S)-2-carboxyindoline or its protic acid salts.

DETAILED DESCRIPTION OF THE INVENTION

The invention in its broadest aspects relates to improved and novel processes for preparing [(2S-(2α,-3aβ,7aβ) -octahydro-1H-2-carboxylic acid and esters thereof. Depending upon the desired end product, slightly different but related process routes may be employed. There are two general reaction schemes which may be employed. According to the first general reaction scheme the starting compound is an acid of the formula III:

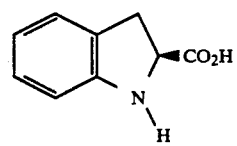

which when reacted according to the processes of this invention results in either the ester or acid of the compound of formula I. In the second general reaction scheme the starting material is an ester of the formula V:

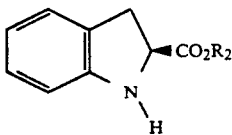

The resulting products are either the ester or acid of the compound of formula I depending upon the particular reaction carried out.

A. First General Reaction Scheme

Processes according to the first general reaction scheme are described hereinafter.

According to one embodiment of the invention a one step process for preparing a compound of the formula (II):

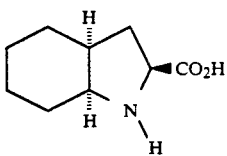

comprises reacting an indoline compound of the formula III:

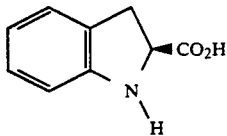

with $H_2$ at a pressure below about 400 psi in a deoxygenated solvent, which is a mixture of water and a compound of the formula, $R_2OH$, where $R_2$ is selected from any of $C_{1-6}$ straight- or branched-chained alkyl or $C_{4-6}$ cycloalkyl. The reaction is carried out in the presence of a precious metal based catalyst containing more than about 5% precious metal based on the weight of the catalyst.

This same compound of formula II may also be prepared in a 2 step procedure comprising reacting the indoline compound of formula (III):

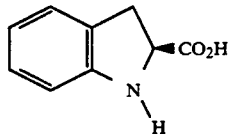

with $H_2$ at a pressure below about 400 psi, in a solvent of the formula, $R_2OH$, which solvent is deoxygenated, contains no more than a minimal amount of water not to exceed about 2%, and is acidified with an acid (HX) such as HCl, $H_2SO_4$, $CF_3CO_2H$ or $H_3PO_4$, wherein X is an anion such as $CL^-$, $HSO_4^-$, $CF_3CO_2^-$ or $H_2PO_4^-$ in an amount in excess of the amount required to protonate the indoline compound. The reaction is carried out in the presence of a precious metal based catalyst containing more than about 5% by weight precious metal, based on the weight of the catalyst. The resulting Product is an acid addition salt of the ester of the formula IV:

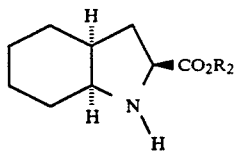

which is then reacted under hydrolytic conditions to produce the desired acid of Formula II.

In the alternative, if the desired end product is the free ester or the acid addition salt of the compound of formula IV it may be separated before undergoing hydrolysis.

B. Second General Reaction Scheme

The compound of formula II may, alternatively, be prepared according to the second general reaction scheme by reacting an indoline compound of the formula (V):

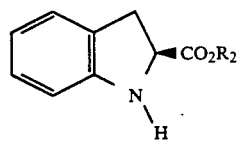

with $H_2$ at a pressure below about 400 psi, in a solvent of the formula, $R_2OH$, which solvent is deoxygenated, contains no more than a minimal amount of water not to exceed about 2%, and is acidified with an amount of acid that is in excess of the amount required to protonate the indoline compound. Again, the reaction is carried out in the presence of a precious metal based catalyst containing more than about 5% by weight precious metal based on the weight of the catalyst. The resulting product is the ester compound of formula IV:

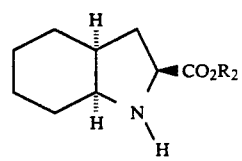

In the alternative, if the desired end product is the free ester or the acid addition salt of the compound of formula IV, it may be separated before undergoing hydrolysis.

In the processes according to the first general reaction scheme, the hydrogenation is preferably effected at a pressure below about 120 psi and most preferably at about 20 to about 60 psi employing as the catalyst (10% rhodium hydroxide on activated carbon, 20% palladium hydroxide on activated carbon, or mixed rhodium hydroxide/palladium hydroxide on activated carbon (10% rhodium hydroxide/10% palladium hydroxide on activated carbon and 5% rhodium hydroxide/5% palladium hydroxide on activated carbon) in an aqueous-alcoholic solvent wherein the alcohol is methanol or ethanol.

In the processes according to the second general reaction scheme, the hydrogenations are preferably carried out at a pressure below about 50 psi, most preferably at about 20 to about 50 psi, employing mixed rhodium hydroxide/palladium hydroxide catalysts, such as 10% rhodium hydroxide/10% palladium hydroxide on activated carbon or 5% rhodium hydroxide/5% palladium hydroxide on activated carbon, wherein the alcohol is either methanol or ethanol.

Products from the first general scheme starting from the compound of formula III and producing the compound of formula II are isolated from the reaction mixture by filtration to remove the catalyst followed by partial removal of the solvents and crystallization from mixtures of water and organic solvents. Suitable organic solvents include ketones and ethereal solvents i.e. acetone, methylethylketone, tetrahydrofuran, glyme and diglyme.

Reaction mixtures giving products of the free ester compounds of general formula IV are filtered to remove catalyst and after evaporation of the solvent(s) the residue is dissolved in water basified with a suitable inorganic base such as an alkali hydroxide (NaOH or KOH) or alkali carbonate ($K_2CO_3$ or $Na_2CO_3$) and the product extracted with a suitable organic solvent such as ether, toluene or ethyl acetate.

Examples of other suitable $R_2OH$ solvents include $C_{1-6}$ straight- or branched-chained alkyl alcohol (e.g., methanol, ethanol, or isopropanol) and $C_{4-6}$ cycloalkyl alcohol (e.g., cyclopropylmethanol or cyclohexanol).

Although the preferred catalysts for carrying out the hydrogenations are recited above, other precious metal based catalyst may be employed. Other such catalysts include iridium on carbon, iridium on alumina powder, Palladium on carbon, palladium & platinum on carbon, palladium on alumina, palladium on barium carbonate, palladium on barium sulfate, palladium on calcium carbonate, palladium on kielselguhr (diatomaceous earth), palladium on silica-alumina, palladium on silica gel, palladium on strontium carbonate, palladium on tin oxide, Palladium on titania, platinum on carbon, platinum on alumina, platinum on barium carbonate, platinum on barium sulfate, platinum on kielselguhr (diatomaceous earth), platinum on silica-alumina, platinum on silica gel, platinum on tin oxide, platinum on titania, rhenium on alumina, rhenium on alumina, rhenium on kielselguhr (diatomaceous earth), rhodium on carbon, rhodium on alumina, rhodium on kielselguhr (diatomaceous earth), rhodium on silica-alumina, rhodium on silica gel, rhodium on titania, ruthenium on carbon, ruthenium on alumina, ruthenium on silica-alumina, ruthenium on silica gel, ruthenium on titania, silver on alumina and silver on titania. The aforesaid precious metal catalyst on carbon are employed either in the inactivated or preferably in the activated forms. In addition, suitable forms in which the catalysts are employed include powder, granules, extrudate, pellets and spheres.

The preferred catalysts employed in this invention are prepared in dry non-pyrophoric forms by known techniques such as described by Pearlman, W., *Tetrahedron Lett.*, 17, 1663 (1967). In particular, precious metal(s) halide (e g , $PdCl_2$ and or $RhCl_2 \cdot 3H_2O$) are combined with carbon (e.g., DARCO G-60) in deionized water and rapidly stirred while being heated to about 80° C. To the heated mixture is added all at once an aqueous solution of LiOH and then the heating is terminated. The mixture is then stirred overnight before it is filtered and then washed with 0.5 v/v% aqueous acetic acid. The collected solid is air dried and then dried under vacuum at about 60° C. This catalyst is then hydrogenated in situ to activate it.

The deoxygenation of the hydrogenation medium is effected by an assortment of standard techniques such as vacuum degassing, Snyder, L. R. et. al. "Introduction to Modern Liquid Chromatography", Wiley, New York, pp 95-97 and 271 (1974) and Bakalyar, S. R., et. al., *J. Chrom.*, 158 (1978) 277, heating as described by Perry, S. G. et. al., "Practical Liquid Chromatography," Plenum, New York, p. 174 (1972), ultrasonic treating as described by Del' Ova, V. E. et. al., *Anal. Chem.*, 48 992 (1976) and Kapustina, O. A. et. al. editors, "Physical Principles of Ultrasonic Technology" 1, Plenum, New York (1973) and sparging as described by Bakalyar, S. R. et. al., *J. Chroma.*, 158 277 (1978).

Sparging, the presently most preferred deoxygenating technique, involves passing an inert gas, preferably helium, at a flow-rate of about 1000 ml/minute in about 100 ml of the hydrogenation solvent for about 15 to about 30 seconds which removes greater than about 95% of the dissolved oxygen.

In the processes which are carried in the solvent of the formula, $R_2OH$, that contains no more than about 2% of water, the minimization of water is effected by using the solvent in its anhydrous form (e.g., absolute ethanol or anhydrous methanol). In addition, the amount of water that is introduced in the acidification of the solvent is minimized by bubbling a dry mineral acid (e.g., HCl) in gaseous form through the solvent or by adding a concentrated form of a mineral acid (e.g., concentrated sulfuric acid) to the solvent.

Hydrolytic conditions for converting the octahydroindole carboxylic acid ester to the corresponding acid are either (i) basic conditions as described by Vincent, M. et. al. Tetrahedron Lett. 23(16), 1677 (1982) and in U.S. Pat. No. 4,508,729 to Vincent, M. et. al. (e.g., using relative to an amount of the ester an equivalent amount of a base such as 0.9 N aqueous sodium hydroxide in an alcohol such as methanol or ethanol (1 ml: 3 to 4 ml at about room temperature for about 20 hours) or (ii) acidic conditions as described Blankley, C. J. et. al., *J. Med. Chem.*, 30, 992 (1987) and in U.S. Pat. No. 4,350,704 to Hoefle, M. et. al. (e.g., about 0.01 mole of the ester is heated to reflux in about 15 ml of 15 weight % of a mineral acid such as hydrochloric acid for about 4 hours).

EXAMPLES

Abbreviations used herein include: TLC, Thin-layer chromatography; HPLC, High Pressure Liquid Chromatography; HOAc, glacial acetic acid; MeOH, methanol; $R_f$ retardation factor.

NMR spectra were obtained with a Brucker AM 400 with tetramethylsilane as an internal standard. Melting points were determined on a Hoover melting point apparatus and are uncorrected.

The enantiomeric purity of [2S-($2\alpha$, $3a\beta$, $7a\beta$)]-octahydro-1H-indole-2-carboxylic acid was determined using chiral HPLC: Waters 600 solvent delivery system; Mobile phase: 0.25 mM $CuSO_4$ at 2 ml/min; Column: 25 cm×4.5 mm Chiralpak WH ® (J. T. Baker) at 50° C.; Detection, Waters 490 UV detector at 240 UV detector nm; Sample injection 50 μl of 10 mg/ml sample dissolved in water; retention time of the title compound, 17.3 min.

EXAMPLE 1

Preparation of
[2S-(2α,3aβ,7aβ)]-octahydro-1H-indole-2-carboxylic acid

A solution of distilled water (50 ml) and methanol (200 ml) was sparged with helium for 1 hour. The deoxygenated solvent was added to the 10% rhodium on carbon catalyst (0.50 g on a dry weight basis, 10% load) and 2S-indoline-2-carboxylic acid (25.0 g, 0.153 mol) in an argon flushed autoclave reactor equipped with an internal baffle. The reactor was alternately evacuated and pressurized with hydrogen to 60 psi four times while stirring the reaction mixture at about 260 rpm. Stirring was stopped and the reactor heated to an internal temperature of 60° C. Stirring at 485 rpm was begun and additional hydrogen introduced to bring the pressure to 80 psi. Hydrogenation was continued for 4.5 hours at 80 psi Heating and stirring were stopped and the reactor allowed to cool to an internal temperature of 20°-30° C. The reactor was evacuated and argon introduced. The reaction mixture was filtered through a filter aid such as diatomaceous earth (DICALITE®) to remove the catalyst and the filter cake washed with methanol. Methanol was removed by rotary evaporation at about 40° to 50° C. The residual solid plus water was placed under an inert gas (i.e. argon) and bis(2-methoxyethyl)ether (diglyme) (50 ml) added. The mixture was heated to 100° C. and distilled water (14 ml) added slowly until all solid dissolved. Heat was removed and the solution allowed to cool to room temperature with stirring. The product began to crystallize while cooling. The mixture (under argon) was refrigerated overnight then filtered by suction. The collected solid was washed with diglyme (25 ml) and dried in air followed by drying in vacuo at 65° C. for 1-2 days to give 3.00 g of [2S-(2α, 3aβ, 7aβ)]-octahydro-1H-indole-2-carboxylic acid (58% yield) as a white solid, mp (265° C.) 270°-272° C. (dec.). This material eluted as one spot by TLC: $R_f$ 0.35 (Whatman MK6F Silica gel plates, 2.5 cm × 7.5 cm × 200 μm layer thickness, eluted with MeOH/CH$_2$Cl$_2$/AcOH 50:50L2). Enantiomeric purity ≧99% enantiomeric excess by HPLC.

EXAMPLE 2

Preparation of
[2S-(2α,3aβ,7aβ-octahydro-1H-indole-2-carboxylic acid and its ethyl ester A solution of absolute ethanol (88 ml) and concentrated H$_2$(1.84 ml) was sparged with argon for 1 hour. The deoxygenated solvent was added to the 10% rhodium/10% palladium on carbon catalyst (0.23 g on a dry weight basis) and 2S-indoline-2-carboxylic acid (5.00 g, 0.0307 mol) in an argon flushed bomb reactor. The reactor was alternately evacuated and pressurized with hydrogen to 80 psi five times while stirring the reaction mixture at about 260 rpm and the reactor was heated to a temperature of 60° C. After 45 minutes, the pressure was increased to 120 psi. The reaction was allowed to proceed for 3 more hours at about 60° C. Heating and stirring were stopped and the reactor was allowed to cool to an internal temperature of 20°-30° C.

An aliquot of the reaction mixture was removed and then filtered through a filter aid (DICALITE®) to remove the catalyst. The filtrate was diluted with water and neutralized with solid potassium bicarbonate. The pH was then adjusted to about 9 with solid potassium carbonate and the aqueous solution was extracted with ethyl acetate. Gas chromatography analysis of the extract disclosed the presence of IV, and the analysis by TLC (TLC solvent = 25% MeOH in CH$_2$Cl$_2$) of organics in the reaction mixture and work-up solution disclosed the presence of II.

EXAMPLE 3

Preparation of ethyl
[2S-(2α,3aβ,7aβ)]-octahydro-1H-indole-2-carboxylate

A solution of absolute ethanol (12.5 ml) and concentrated H$_2$SO$_4$ (0.4 ml) was sparged with argon for 30 minutes. This solution was added to the 10% rhodium on carbon catalyst (51 mg) and ethyl 2S-indoline-2-carboxylate hydrochloride (1.5 g, 6.59 mmol) in an argon flushed Parr bottle reactor. The reactor was alternately evacuated and pressurized with hydrogen to 40 psi four times, and then shaken while the reactor was heated to a temperature of 60° C. The pressure rose to 49.5 psi. The heating and shaking were stopped after 23.5 hours.

An aliquot of the reaction mixture was removed and worked-up as described in Example 2. Gas chromatographic analysis of the resultant extract disclosed a 10% yield of IV.

An additional 51 mg of the catalyst, which was wet with approximately 5 ml of absolute ethanol, was added to the reaction mixture, and the hydrogenation was reinitiated at 60° C. for 40 hours. An aliquot of this reaction mixture was worked-up as described in Example 2 and the gas chromatographic analysis of the resultant extract disclosed a 21% yield of the IV.

EXAMPLE 4

Preparation of ethyl
[2S-(2α,3aβ,7aβ)]-1H-octahydro-indole-2-carboxylate

After a solution of absolute ethanol (12.5 ml) and concentrated H$_2$SO$_4$ (0.4 ml) was sparged as in Example 3, the solution was added to a hydrogenation reactor containing 10% rhodium/1% palladium on carbon catalyst (51.5 mg) and ethyl 2S-indoline-2-carboxylate hydrochloride (1.5 g, 6.59 mmol) and reacted as in Example 3 for 23.5 hours. The analysis of an aliquot of this reaction mixture disclosed a 32.9% yield of IV.

An additional 101.6 mg of catalyst was added and the hydrogenation was resumed at 60° C. for 44 hours. An analysis of an aliquot of the reaction mixture disclosed that the reaction had gone to completion. The solvent was removed by evaporation, and the residue was diluted with water and neutralized with KHCO$_3$. Solid K$_2$CO$_3$ was added to pH of about 8 and the mixture was extracted 2 times with ethyl acetate. The combined organics were washed with brine, dried over Na$_2$SO$_4$, filtered and concentrated to yield 0.70 g (54%) of the crude product as an oil. $^1$H NMR: CDCL$_3$ δ(TMS) 1.1-1.8 (12H,m); 2.0(1H; 2.2(2HO; 3.1(1H); 3.8(1H); 4.3(2H).

EXAMPLE 5

Preparation of [2S-(2α, 3aβ, 7aβ)]-1H-octahydro-indole-2-carboxylic acid

The ethyl [2S-(2α, 3aβ, 7aβ)]-1H-octahydroindole-2-carboxylate compound is hydrolyzed according to the method disclosed by Blankley et. al. (*J. Med. Chem.*, 30, 992, 997 (1987). The hydrolysis is effected as follows: a solution of 2.0 g (0.01 mol) of the product of Example 4 in 25 ml of 15% HCl is heated at reflux for 4 hours and then evaporated to dryness in vacuo to yield after recrystallization from acetonitrile/ethyl acetate 1.7 g of the hydrochloride salt, mp 186°-187° C. dec.

The free acid is obtained by dissolving 1.2 g of the hydrochloride in 10 mL of $H_2O$ and adding 2 N NaOH to pH 6.5. The resulting solution is evaporated to dryness under reduced pressure and the residue then refluxed with 50 mL of acetonitrile and filtered hot. Concentration of the filtrate to 10 mL and cooling gives 0.5 g of the titled product. Physical data regarding the product is disclosed by Vincent et. al. (*Tetrahedron Lett.* 23(16), 1677, 1679, (1982)) as follows: $[\alpha]20.5°_D = -47.7$, (C =1, MeOH); mp 268°-271° dec.

We claim:

1. A process for stereospecifically preparing a compound of the formula II

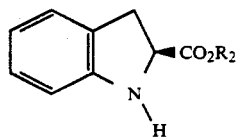

(V)

comprising the substantially pure single enantiomer [2S-(2α, 3aβ, 7aβ)-octahydro-1H-indole-2-carboxylic acid, whereby the process comprises the step of:

(a) reacting an indoline compound of the formula III

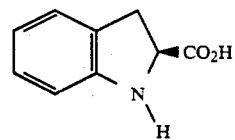

(III)

with $H_2$ at a pressure below about 400 psi in a deoxygenated solvent, which is a mixture of water and a compound of the formula, $R_2OH$ containing a precious metal based on the weight of the catalyst, wherein $R_2$ is a $C_{1-6}$ straight- or branched-chained alkyl or $C_{4-6}$ cycloalkyl.

2. The process of claim 1 wherein the pressure is below 120 psi, the catalyst is 10% rhodium hydroxide on activated carbon, 20% palladium hydroxide on activated carbon, 10% rhodium hydroxide/10% palladium hydrozide on activated carbon, 5% rhodium hydroxide/5% palladium hydroxide on activated carbon, or 10% rhodium hydroxide/1% palladium or activated carbon and $R_2$ is methyl or ethyl.

3. The process of claim 2 wherein the catalyst is 10% rhodium/10% palladium hydroxide on activated carbon.

4. A process for stereospecifically preparing a compound of the formula IV

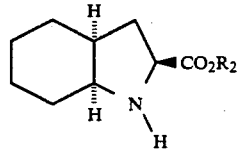

(IV)

comprising the substantially pure single enantiomer of an ester of [2S-(2α, 3aβ, 7aβ)]-octahydro-1H-indole-2-carboxylic acid wherein $R_2$ is a $C_{1-6}$ straight- or branched-chained alkyl, $C_{4-6}$ acycloalkyl, phenyl or $C_{1-6}$ straight- or branched-chained alkylphenyl, comprising the step of:

(a) reacting an indoline compound of the formula III

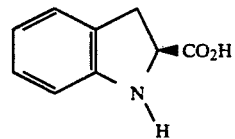

(III)

with $H_2$ at a pressure below about 400 psi in a deoxygenated and acidified solvent of the formula, $R_2OH$, containing a precious metal based catalyst containing more than about 5% precious metal based on the weight of the catalyst, wherein $R_2$ is a $C_{1-6}$ straight- or branched-chained alkyl or $C_{4-6}$ cycloalkyl.

5. The process of claim 4 wherein the pressure is below 120 psi, the catalyst is 10% rhodium hydroxide on activated carbon, 20% palladium hydrozide on activated carbon, 10% rhodium hydroxide/10% palladium hydroxide on activated carbon or 5% rhodium hydroxide/5% palladium hydroxide on activated carbon and $R_2$ is methyl or ethyl.

6. A process for stereospecifically preparing a compound of the formula IV

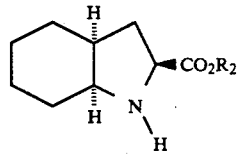

(IV)

comprising the substantially pure single enantiomer of an ester of [2S-(2α, 3aβ, 7aβ)]-octahydro-1H-indole-2-carboxylic acid wherein $R_2$ is a $C_{1-6}$ straight- or branched-chained alkyl, $C_{4-6}$ cycloalkyl, comprising the step of:

(a) reacting an indoline compound of the formula V

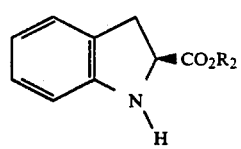

(V)

with $H_2$ at a pressure below about 400 psi in a deoxygenated and acidified solvent of the formula, $R_2OH$, containing a precious metal based catalyst containing more than about 5% precious metal based on the weight of the catalyst, wherein $R_2$ is a $C_{1-6}$ straight- or branched-chained alkyl or $C_{4-6}$ cycloalkyl.

7. The process of claim 6 wherein the pressure is below 50 psi, the catalyst is 10% rhodium hydroxide/10% palladium hydroxide on activated carbon or 5% rhodium hydroxide/5% palladium hydroxide on activated carbon and $R_2$ is methyl or ethyl.

* * * * *

UNITED STATES PATENT AND TRADEMARK OFFICE
CERTIFICATE OF CORRECTION

PATENT NO. : 5,258,525
DATED : November 2, 1993
INVENTOR(S) : Maryanoff et al.

It is certified that error appears in the above-indentified patent and that said Letters Patent is hereby corrected as shown below:

Column 9, line 20, change structure designated by (V) to same structure designated as (II) at Column 3 line 20.

Column 9, line 25, add --]-- after "7aβ)"

Col. 9, line 40, claim 1(a) add --catalyst containing more than about 5% precious metal based-- after "precious metal based"

Col. 9, line 47, change "hydrozide" to --hydroxide--

Col. 9, line 49, change "or" to --on--

Col. 9, line 24, change "hydrozide" to --hydroxide--

Signed and Sealed this

Twenty-fourth Day of May, 1994

Attest:

BRUCE LEHMAN

*Attesting Officer*  *Commissioner of Patents and Trademarks*